United States Patent [19]  
Davies et al.

[11] 4,024,864  
[45] May 24, 1977

[54] INJECTOR WITH OVERSPEED PROTECTOR

[75] Inventors: Gomer L. Davies, Fort Lauderdale; Ira R. Baker, Miami, both of Fla.

[73] Assignee: Cordis Corporation, Miami, Fla.

[22] Filed: Sept. 5, 1975

[21] Appl. No.: 610,566

[52] U.S. Cl. .................. 128/214 F; 128/DIG. 7; 128/DIG. 13; 417/20; 417/45

[51] Int. Cl.² .................................. A61M 5/00

[58] Field of Search ............ 128/2 A, 2 R, 214 E, 128/214 F, DIG. 7, DIG. 12, DIG. 13; 417/20, 22, 43, 44, 45

[56] References Cited  
UNITED STATES PATENTS 3,623,474 11/1971 Hellman et al. ............... 128/2 A  
3,731,679 5/1973 Wilhelmson et al. ......... 128/214 F Primary Examiner—William E. Kamm  
Attorney, Agent, or Firm—Kenway & Jenney

[57] ABSTRACT

A flow rate controlled angiographic injection system is provided with an overspeed injection protection means. The injection system includes a motor driven syringe injector and a flow rate controller responsive to the overspeed protection means to drive the motor to inject a contrast medium from the syringe into a blood vessel at a desired flow rate when the actual flow rate from the syringe is less than or equal to the predetermined flow rate, and to disable the motor otherwise. The overspeed injection protection means includes a means for generating a signal representative of the actual flow rate of a contrast medium from the syringe by detecting the back emf induced in the motor armature, compensation being made for the resistive voltage drop in the armature windings and brushes.

3 Claims, 2 Drawing Figures

INJECTOR WITH OVERSPEED PROTECTOR

BACKGROUND OF THE INVENTION

This invention relates to angiography and more particularly, to means for controlling the injection rate of a radio-opaque fluid into the vascular system for radiological analysis.

It is well known that certain angiographic procedures require the repetitive injection of precise volumes of radio-opaque fluids at certain body locations at precisely controlled rates. For many of these procedures, protection against fluid injector malfunction is essential for patient's safety, since excessive pressure may rupture the catheter and excessive volume may produce severe allergenic reactions.

In order to achieve a measure of the desired flow rate and volume control, the prior art angiographic injector systems generally include motor driven syringe and a flow rate control feedback loop which operates to control either in the syringe plunger position or velocity in a manner reducing the error of that parameter from the required value to achieve the desired flow rate. Control of the flow rate is particularly important, since many prior art systems utilized a flow rate and time product network to yield a measure of volume and thus, excessive flow rate may result in excessive volume. In controlling the flow rate, these systems generally utilize a tachometer generator coupled to the syringe drive motor for producing a signal representative of the motor speed (which is proportional to the fluid flow rate from the syringe).

A deficiency of such systems is the response time of the flow rate control loop which in many cases provides inadequate protection against short term excursions of the flow rate from a desired nominal value. Furthermore, the use of a discrete tachometer generator for providing the actual flow rate signal adds to the bulk of the instrumentation associated with the injector system.

Accordingly, it is an object of the present invention to provide an injector system having a controlled flow rate injection capability but further having protection against excessive flow rate.

It is a further object of this invention to provide an angiographic injector with a flow rate control means responsive to an overspeed injection protection means.

It is still another object to provide an angiographic injection system, a flow rate injector system having overspeed protection using an improved flow rate detector.

SUMMARY OF THE INVENTION

According to the present invention, a flow rate controlled angiographic injector is provided with an overspeed injection protection means. The injector includes a syringe having a reservoir for storing a contrast medium and having a plunger for injecting that medium into a blood vessel. The injector further includes a motor and an associated plunger coupling means for driving the plunger in response to a motor drive signal.

A flow rate controller provides a motor drive signal in response to a binary protection control signal. When the protection control signal is representative of a first state, the flow rate controller generates a motor drive signal which is related to the difference between the actual flow rate of contrast medium from the syringe and a desired flow rate. When the protection control signal is representative of the other binary state, the flow rate controller disables the motor, thereby preventing further injection.

The overspeed protection means includes a means for generating a signal representative of the actual flow rate of the contrast medium by detecting the back emf induced in the armature of the motor. The overspeed injection protection means further includes a means for comparing the actual flow rate signal with a signal representative of a predetermined flow rate, and then generating said binary protection control signal. The protection control signal is representative of the first binary state when the actual flow rate is less than or equal to the predetermined flow rate, and representative of the other binary state otherwise.

Using this method of generating a motor speed signal eliminates the need for a discrete tachometer generator. Furthermore, according to the present invention, the overspeed protection means which monitors the actual flow rate is effective to immediately interrupt the flow rate control loop by disabling the motor, irrespective of the response time of that loop, when the actual flow rate exceeds the predetermined flow rate.

BRIEF DESCRIPTION OF THE DRAWINGS

The foregoing and other objects of this invention, the various features thereof, as well as the invention itself, may be more fully understood from the following description, when read together with the accompanying drawings, in which.

DESCRIPTION OF THE PREFERRED EMBODIMENT

Figure 1:
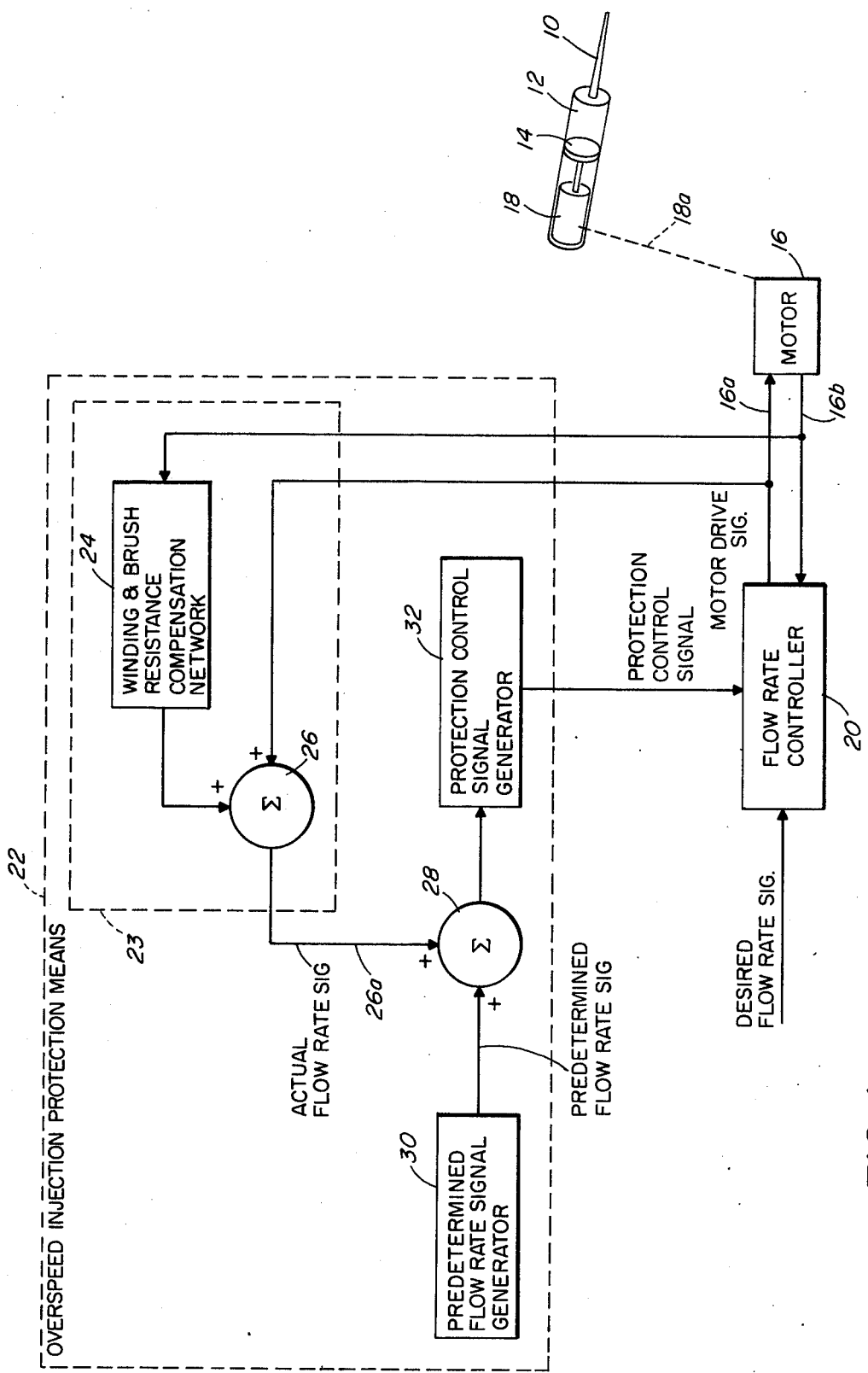
FIG. 1 shows in block diagram form an embodiment of an angiographic injector with an overspeed injection protection means in accordance with the present invention.

An embodiment of the present invention is shown in FIG. 1 to include an injector having a syringe 10 with a reservoir 12 for storing a radio-opaque contrast medium. The injector further has a plunger 14 and a motor 16 connected thereto by a mechanical coupling means 18 and broken line 18a for driving the plunger 14 through reservoir 12 to inject the contrast medium into a blood vessel. The motor 16 is a shunt-excited or permanent magnet d.c. motor. The lines 16a and b as illustrated in FIG. 1 are representative of the connections across the armature of motor 16. It will be understood that the injector shown in FIG. 1 is merely exemplary and alternatively, any one of many suitable type injectors known in the art may be used.

The embodiment of FIG. 1 further includes a flow rate controller 20 for generating a motor drive signal which in turn is applied to motor 16 for controlling the motion of the plunger 14 and the injection of the contrast medium via syringe 10. The flow rate control means 20 includes a means responsive to an applied protection control signal, which is effective to cause controller 20 to generate a drive signal and apply that drive signal to motor 16 by way of the line 16a. The drive signal is related to the difference between the actual flow rate of the contrast medium from the syringe 10 and the predetermined desired flow rate when the binary control signal is representative of a first binary state, and is a disabling signal (i.e. equal to a current, such as zero amps, effective to disable the motor when the binary control signal is representative of a second binary state. When the binary control signal is representative of the first state, the flow rate controller 20 may utilize any suitable control means known in the art which utilizes a feedback signal from the motor indicative of the motor speed to adjust the motor speed so that the actual flow rate of contrast medium from syringe 10 matches a predetermined desired flow rate.

The angiographic injection system of FIG. 1 also includes an overspeed injection protector 22. Protector 22 includes a generating means 23 for generating an actual flow rate signal representative of the actual flow rate of contrast medium from syringe 10. This signal is generated from a signal representative of the potential drop across the armature of motor 16 as measured across line 16a and 16b. The voltage across lines 16a and 16b includes a voltage drop equal to the sum of (1) the product of the armature current and the sum of the motor winding and brush resistance, and (2) an induced voltage (the back emf) generated in the motor 16. This back emf is proportional to the motor speed and thus, is a measure of the actual flow rate of contrast medium through syringe 10. Generating means 23 includes a winding and brush resistance compensation network 24 which generates a signal proportional to the current drawn by motor 16, i.e. including the sum of the potential drops across the windings and brushes of motor 16. The summation network 26 generates the actual flow rate signal by subtracting the signal representative of the armature voltage drop due to the winding and brush resistances (as generated by winding and brush resistance compensation network 24) from the signal on line 16a (measured with respect to ground and which is representative of the level of energization of motor 16, including the winding and brush potential drops and the back emf).

The resultant output signal from network 26, representative of the back emf induced in the armature winding, is applied to a first input of the summation network 28. The predetermined flow rate signal generator 30 applies a predetermined signal to the other input of network 28. This latter signal is selected by an operator to be representative of a maximum rate at which the contrast medium may be injected by the system. Network 28 generates a signal equal to the difference between the actual flow rate signal and the predetermined flow rate signal. The difference signal generated by the network 28 is applied to a protection control signal generator 32 which generates the binary protection control signal generator 32 which generates the binary protection control signal for application to the flow rate controller 20.

The control signal produced by generator 32 is representative of a first binary state when the actual flow rate is less than or equal to the predetermined flow rate and the binary control signal is representative of the second binary state otherwise.

In operation, an operator-selected desired injection flow rate signal is applied to the input of flow rate controller 20 which drives motor 16 and, in turn, the plunger 14 to inject a contrast medium from reservoir 12 through syringe 10 into a blood vessel at or near the desired flow rate. However, the operation of the flow rate controller motor and injector is continually monitored by the overspeed injection protector 22 which detects when the flow rate from syringe 10 equals or exceeds a predetermined flow rate and, in response thereto, generates a binary control signal which disables the motor 16, thereby interrupting injection. At all times when the injection flow rate is less than the predetermined flow rate, injection of the contrast medium proceeds under the control of the flow rate controller 20.

The flow rate controller 20 and motor 16 and associated feedback control network may be one of many forms well known in the art. More particularly, for example, the motor might be controlled by a silicon controlled rectifier (SCR) network and may have a tachometer motor speed sensor attached to the motor for generating a signal representative of the motor speed (and thus, the actual flow rate). Alternatively, the motor speed and, thus, the actual flow rate speed may be generated by a back emf detector (similar to that described above for use in the overspeed injection protector 22) wherein the effective armature and brush resistance for the motor 16 is determined experimentally, and an appropriate compensation signal is generated by passing the motor armature current through an appropriate resistor.

Figure 2:
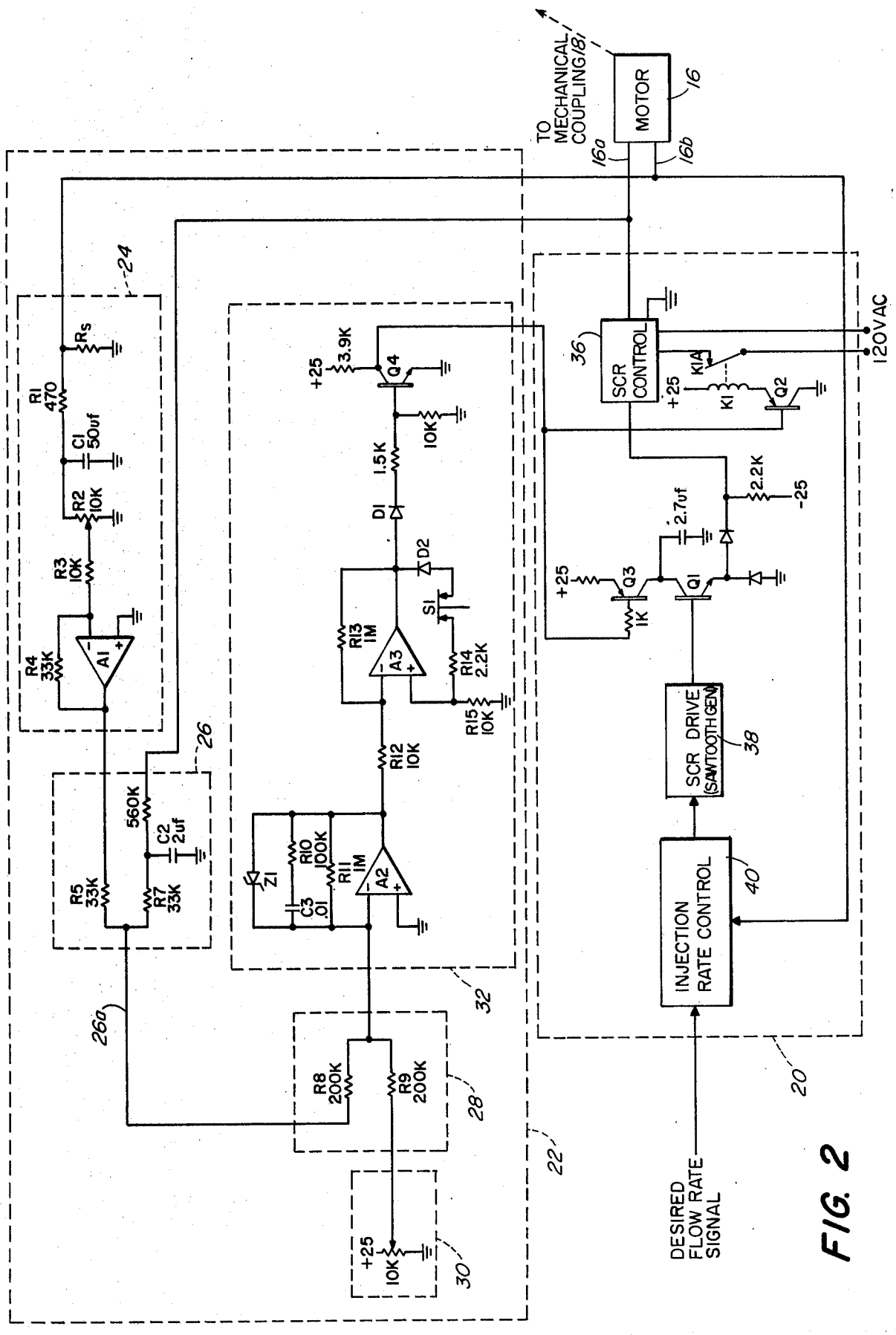
FIG. 2 shows in schematic form an exemplary circuit for the embodiment of FIG. 1.

FIG. 2 shows an exemplary circuit configuration for the embodiment of FIG. 1. The flow rate controller 20 is illustrated in part showing an SCR control 36, which produces the motor drive signal on line 16a by modulating an applied 120 volt a.c. signal in accordance with an SCR trigger signal from the transistor Q1. The input to the base of transistor Q1 is provided by an SCR drive sawtooth generator 38, which, in turn, is driven by an injection rate control network 40 from a desired flow rate signal provided by the operator. Detailed schematic diagrams for blocks 36, 38 and 40 are not shown in FIG. 2 since any one of many well known prior art circuits may be used in this configuration.

The transistor Q2 provides a binary switching function for the power relay K1 in response to the binary protection control signal, wherein contacts K1-A pass a 120 volt a.c. signal to SCR control 36 when closed. When the binary protection control signal provided by overspeed injection protector 22 is near ground potential, transistor Q2 is switched to its conductive state, thereby energizing relay K1 and closing contacts K1-A. When protection control signal is substantially positive, indicating excess injection speed, transistor Q2 is in its non-conductive state. Consequently, the relay K1 is not energized and contacts K1-A are open, thereby preventing overspeed injection by de-energizing motor 16, even in the event of short circuited SCR's in control 36.

Transistor Q3 is connected in a "wired and" circuit configuration, and is also switched by the binary control signal produced by protector 22. When switched to its conductive state, Q3 permits transistor Q1 to pass the sawtooth signal applied from drive network 38 to the SCR control 36. When the protection control signal is substantially positive, indicating excessive injection speed, transistor Q3 is in its non-conductive state, thereby preventing transistor Q1 from passing the sawtooth signal to SCR control 36.

Thus, when the motor 16 produces an actual flow rate less than the predetermined flow rate, the binary protection control signal applied to controller 20 is near ground potential, turning ON both transistors Q2 and Q3, permitting passage of the SCR trigger signal via transistor Q1 to SCR control 36, and closing contacts K1-A. When the actual flow rate exceeds the predetermined flow rate, the protection control signal is substantially positive, turning OFF both transistors Q2 and Q3, interrupting the passage of the SCR trigger signal and the 120 volt a.c. signal to SCR control 36.

In the overspeed injection protector 22, the resistor $R_s$ is configured so that substantially all of the motor 16 armature current passes therethrough, thereby providing a voltage at the input to the winding and brush resistance compensation network 24 (resistors R1–R4, capacitor C1 and amplifier A1) which is proportional to the winding and brush resistance of motor 16. Network 24 scales this voltage to be the negative of the portion of the drop across the armature of motor 16 due to the winding and brush resistance. The summation network 26 (resistors R5–R7 and capacitor C2) adds this signal to the signal representing the total voltage across the armature, as applied from line 16a, resulting in a signal on line 26a which is proportional to the motor speed, or alternatively, the actual rate of flow of the contrast medium through the syringe 10. This actual flow rate signal is applied to a first input of summation network 28.

The signal generator 30 provides a predetermined flow rate signal for the second input of network 28. This latter signal is representative of the maximum flow rate which is permitted to be provided by the injector system. It should be noted that this generator 30 may be coupled to the same operator control which generates the desired flow rate signal for use by the flow rate control 20. In such an application, the generator 30 would provide a signal which is a predetermined proportion of the desired flow rate, permitting a margin of error satisfactory for patient safety.

In the configuration of FIG. 2, the respective polarities of the predetermined flow rate and the actual flow rate signals are appropriately determined so that the summation network 28 provides at its output a signal representative of the difference between the actual flow rate and the predetermined flow rate, wherein the difference signal is positive when the actual flow rate exceeds the predetermined flow rate and negative otherwise. This difference signal is applied to an input of amplifier A2 in the protection control signal generator 32.

When the actual flow rate exceeds the predetermined flow rate, the output of amplifier A2 swings negative. The zener diode Z1 prevents the output from amplifier A2 from becoming more negative than −3 volts. In response to the negative signal from amplifier A2 (in the range 0 to −3 volts), the output of the high gain amplifier A3 swings positive, forward biasing diode D1 which in turn switches the transistor Q4 to its conductive state. When transistor Q4 is ON, the protection control signal is near ground potential and, as described in the above, transistors Q2 and Q3 are switched to be in their conductive states so that the SCR control 36 drives the motor 16 and in turn, the injector means.

When the actual flow rate exceeds the predetermined flow rate (indicating overspeed injection), the output of amplifier A2 swings positive. The response time of amplifier A2 is controlled by the capacitor C3 and resistor R10 to prevent line transients from triggering this circuit, and also to prevent motor cogging from falsely indicating overspeed.

In response to the positive voltage applied from amplifier A2, the output of amplifier A3 swings negative, cutting off diode D1 and, in turn, transistor Q4, and transistors Q2 and Q3 and motor 16. In addition, the negative voltage applied from amplifier A3 establishes the positive feedback loop around A3 through diode D2, resistors R14 and R15 and the normally closed contacts of switch S1.

In response to the activation of this feedback loop, amplifier A3 "latches" with its output at a level more negative than −3 volts. Due to the reduction of the actual flow rate to zero following motor 16 shut down, the output of amplifier A2 swings negative but due to the action of zener diode Z1 noted above, this signal never becomes more negative than −3 volts. Consequently, it is ineffective to change the output of amplifier A3 which maintains its negative output voltage, keeping diode D1 and transistors Q4, Q2, and Q3 non-conductive, and the motor 16 disabled. The operator may reset amplifier A3 by opening the contacts of switch S1, thereby interrupting the positive feedback loop around A3, and permit continued injection of the contrast medium as long as the actual flow rate remains below the predetermined rate.

It will be understood that the configuration described in conjunction with FIG. 2 is merely exemplary and that other embodiments may utilize different circuit configurations in keeping with the present invention. For example, other configurations may include control means for ensuring gradual energization of the injector motor to prevent whipping of the catheter tip. Such control means are described in U.S. Pat. No. 3,674,009, to Donald E. Williamson, and assigned to the assignee of the present invention.

The invention may be embodied in still other specific forms without departing from the spirit or essential characteristics thereof. The present embodiments are therefore to be considered in all respects as illustrative and not restrictive, the scope of the invention being indicated by the appended claims rather than by the foregoing description, and all changes which come within the meaning and range of equivalency of the claims are therefore intended to be embraced therein.

We claim:

1. A flow rate controlled angiographic injector with an overspeed injection protection means comprising, in combination:
    A. an injector means including a syringe having a plunger and having a reservoir connected thereto for storing a contrast medium for injection into a blood vessel, and including a d.c. motor and plunger coupling means for driving said plunger to inject said contrast medium into a blood vessel, said motor being responsive to a motor drive signal,
    B. a flow rate control means responsive to a binary control signal to generate said motor drive signal, said drive signal being related to the difference between the actual flow rate of said contrast medium from said syringe and a desired flow rate when said control signal is representative of a first binary state, and being equal to a disabling signal for said motor when said control signal is representative of a second binary state, and
    C. an overspeed injection protection means including:
        i. means for generating an actual flow rate signal representative of the actual flow rate of said contrast medium from said syringe, said actual flow rate signal generating means including means for subtracting a signal representative of the voltage across the armature of said motor from a signal representative of the product of the armature current and the armature and brush resistances, ii. means for generating a predetermined flow rate signal representative of a predetermined flow rate of said contrast medium from said syringe, and iii. means for generating said binary control signal, said control signal being representative of said first binary state when said actual flow rate is less than or equal to said predetermined flow rate, and said second binary state otherwise.

2. Angiographic apparatus comprising:

injector means, including a d.c. motor, for injecting contrast medium at a rate essentially proportional to the speed of said motor;

power control means for variably energizing said motor, said control means having a first state in which said motor is energized at a selectable level and a second state in which said motor is de-energized;

feedback means for adjusting the level of energization provided by said control means to maintain a preselectable speed of said motor when said control means is in said first state;

means for sensing the level of energization of said motor and for providing a first signal, which first signal is proportional to said level;

means for sensing the current drawn by said motor and for providing a second signal, which second signal is proportional to said current;

means for combining said signals to provide a rate signal which varies as a function of the back emf of said motor and which represents the rate of injection being provided by said apparatus;

mean providing a limit signal which represents a desired rate limit for injection; and means responsive to said rate and limit signals for setting said control means to said second state when the rate of injection exceeds said desired rate limit.

3. Apparatus as set forth in claim 1 wherein said control means is manually resettable from said second state to said first state.

* * * * *